(12) United States Patent
Calhoun et al.

(10) Patent No.: US 9,410,170 B2
(45) Date of Patent: Aug. 9, 2016

(54) METHODS OF IN VITRO PROTEIN SYNTHESIS

(75) Inventors: Kara Calhoun, Mountain View, CA (US); Michael Christopher Jewett, Kgs. Lyngby (DK); James Robert Swartz, Menlo Park, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 1905 days.

(21) Appl. No.: 10/579,711

(22) PCT Filed: Nov. 18, 2004

(86) PCT No.: PCT/US2004/038830
§ 371 (c)(1),
(2), (4) Date: Feb. 27, 2007

(87) PCT Pub. No.: WO2005/052117
PCT Pub. Date: Jun. 9, 2005

(65) Prior Publication Data
US 2007/0154983 A1 Jul. 5, 2007

Related U.S. Application Data

(60) Provisional application No. 60/524,374, filed on Nov. 20, 2003.

(51) Int. Cl.
C12P 21/06 (2006.01)
C12P 19/34 (2006.01)
C12P 21/02 (2006.01)

(52) U.S. Cl.
CPC *C12P 19/34* (2013.01); *C12P 21/02* (2013.01)

(58) Field of Classification Search
None
See application file for complete search history.

(56) References Cited

U.S. PATENT DOCUMENTS

| | | | |
|---|---|---|---|
| 6,168,931 B1 * | 1/2001 | Swartz et al. | 435/68.1 |
| 6,337,191 B1 * | 1/2002 | Swartz et al. | 435/6 |
| 2002/0168706 A1 | 11/2002 | Chatterjee et al. | |
| 2003/0113778 A1 * | 6/2003 | Schulte et al. | 435/6 |

FOREIGN PATENT DOCUMENTS

WO     03/038117     5/2003

OTHER PUBLICATIONS

"Exogenous." Merriam-Webster Online Dictionary. 2009. Merriam-Webster Online. Nov. 10, 2009, 2 pgs <http://www.merriam-webster.com/dictionary/EXOGENOUS>.*
Nucleotide—definition from Biology-Online.org accessed Nov. 10, 2009, 2pgs http://www.biology-online.org/dictionary/Nucleotide.*
Nucleoside—definition from Biology-Online.org accessed Nov. 10, 2009, 1pg http://www.biology-online.org/dictionary/Nucleoside.*
Calhoun I "Energizing Cell-Free Protein Synthesis With Glucose Metabolism" Biotechnology and Bioengineering, vol. 90, No. 5, Jun. 5, 2005, p. 606-613.*
Calhoun II "An Economical Method for Cell-Free Protein Synthesis using Glucose and Nucleoside Monophosphates" Biotechnol. Prog. 2005, 21, 1146-1153.*
Zubay, G., "In vitro synthesis of protein in microbial systems," (1973) *Annual Review of Genetics*, vol. 7, pp. 267-287.
Stryer, L., "Stoichiometry of the citric acid cycle," (1995) *Biochemistry*, 4th ed.
Kim; et al., "Regeneration of Adenosine Triphosphate from Glycolytic Intermediates for Cell-Free Protein Synthesis", Biotechnology and Bioengineering (2001), 74(4):309-316.

* cited by examiner

*Primary Examiner* — Thane Underdahl
(74) *Attorney, Agent, or Firm* — Pamela J. Sherwood; Bozicevic, Field & Francis LLP (57) ABSTRACT

Improved methods are provided in vitro synthesis of biological molecules, providing for improved yields, lowered costs, and enhanced utility. Improved yield and lowered cost is obtained by the use of a phosphate free energy source in the presence of exogenous phosphate, and optionally in the absence of exogenous nucleoside triphosphates.

13 Claims, 10 Drawing Sheets

Figure 1: Protein produced in cell-free reactions

Figure 2: Addition of phosphate to cell-free reactions using glucose as energy source Figure 3: Important components for successful cell-free reactions using glucose

METHODS OF IN VITRO PROTEIN SYNTHESIS

BACKGROUND OF THE INVENTION

The directed synthesis of biological macromolecules is one of the great achievements of biochemistry. With the advent of recombinant DNA (rDNA) technology, it has become possible to harness the catalytic machinery of the cell to produce a desired protein. This can be achieved within the cellular environment or in vitro using extracts derived from cells.

Cell-free protein synthesis offers several advantages over conventional, in vivo, protein expression methods. Cell-free systems can direct most, if not all, of the metabolic resources of the cell towards the exclusive production of one protein. Moreover, the lack of a cell wall and membrane components in vitro is advantageous since it allows for control of the synthesis environment. For example, tRNA levels can be changed to reflect the codon usage of genes being expressed. The redox potential, pH, or ionic strength can also be altered with greater flexibility than in vivo since we are not concerned about cell growth or viability. Furthermore, direct recovery of purified, properly folded protein products can be easily achieved.

In vitro translation is also recognized for its ability to incorporate unnatural and isotope-labeled amino acids as well as its capability to produce proteins that are unstable, insoluble, or cytotoxic in vivo. In addition, cell-free protein synthesis may play a role in revolutionizing protein engineering and proteomic screening technologies. The cell-free method bypasses the laborious processes required for cloning and transforming cells for the expression of new gene products in vivo, and is becoming a platform technology for this field.

Despite all of the promising features of cell-free protein synthesis, its practical use and large-scale implementation has been limited by several obstacles. Paramount among these are short reaction times and low protein production rates, which lead to poor yields of protein synthesis and excessive reagent cost. Additionally, expensive reagents are required, and conventional methods are inefficient in the use of these expensive reagents.

Particularly useful reactions combine in vitro transcription and translation, thereby providing a direct link between a DNA coding sequence and the protein product. However, the additional requirement for reagents to produce mRNA add to the overall cost of the reaction. Recent publications have discussed many different strategies for cost reduction of in vitro transcription reactions, including reusing DNA templates and employing fed batch protocols. For example, see Kern and Davis (1997) "Application of Solution Equilibrium Analysis to in-Vitro RNA Transcription" *Biotechnology Progress* 13:747-756; Kern and Davis (1999) "Application of a Fed-Batch System to Produce RNA by In-Vitro Transcription" *Biotechnology Progress* 15:174-184.

Improvements are required to optimize in vitro transcription/translation systems. The continuous removal of the inhibitory by-product(s) as well as the continuous supply of substrates for synthesis may enable continuous or semicontinuous reaction systems to support synthesis over long reaction periods. However, these approaches may also result in inefficient use of substrates and therefore in high costs. Elucidation of inhibitory products, and prevention of their synthesis is of great interest for development of in vitro synthetic systems. Also important is the reduction of reagent costs. With present technology, the major reagent costs include the source of chemical energy, enzymes, DNA template, and NTPs. Methods of decreasing these costs while enhancing yield are of great interest.

Relevant Literature

U.S. Pat. No. 6,337,191 B1, Swartz et al. Kim and Swartz (2000) *Biotechnol Prog.* 16:385-390; Kim and Swartz (2000) *Biotechnol Lett.* 22:1537-1542; Kim and Choi (2000) *J Biotechnol.* 84:27-32; Kim et al. (1996) *Eur J Biochem.* 239: 881-886; Kim and Swartz (2001) *Biotechnol Bioeng* 74:309-316; Davanloo et al., *Proc Nat'l Acad Sci USA* 81:2035-2039 (1984); Datsenko et al., *Proc Nat'l Acad Sci USA* 97:6640-6645 (2000); Jewett et al. (2002) Prokaryotic systems for in vitro expression, in *Gene Cloning and Expression Technologies* (Weiner, M. P. and Lu, Q.: eds.), Eaton Publishing, Westborough, Mass., pp. 391-411; Spirin et al., *Science* 242:1162-1164 (1988).

Cunningham and Ofengand (1990) *Biotechniques* 9:713-714 suggest that adding inorganic pyrophosphatase results in larger reaction yields by hydrolyzing the pyrophosphate that accumulates. Pyrophosphate is inhibitory because the pyrophosphate complexes with the free magnesium ions leaving less available for the transcription reaction.

Breckenridge and Davis (2000) *Biotechnology Bioengineering:* 69:679-687 suggest that RNA can be produced by transcription from DNA templates immobilized on solid supports such as agarose beads, with yields comparable to traditional solution-phase transcription. The advantage of immobilized DNA is that the templates can be recovered from the reaction and reused in multiple rounds, eliminating unnecessary disposal and significantly reducing the cost of the DNA template.

U.S. Pat. No. 6,337,191 describes in vitro protein synthesis using glycolytic intermediates as an energy source; and U.S. Pat. No. 6,168,931 describes enhanced in vitro synthesis of biological macromolecules using a novel ATP regeneration system.

SUMMARY OF THE INVENTION

Improved methods are provided for the in vitro synthesis of biological molecules, providing for improved yields, lowered costs, and enhanced utility. Improved cell-free protein synthesis reactions utilize a phosphate-free energy source for ATP production, including, for example, glucose, glutamate, pyruvate, etc. Nucleoside triphosphates are optionally replaced with nucleoside monophosphates. These improvements drastically decrease costs and increase the robustness of cell-free protein synthesis reactions. The reaction is substantially improved by the addition of exogenous phosphate.

DETAILED DESCRIPTION OF THE EMBODIMENTS

Improved methods are provided for the in vitro synthesis of biological macromolecules, providing for improved yields, lowered costs, and enhanced utility. Improved yield and lowered cost is obtained by a combination of reaction conditions, which include, without limitation, the use of a phosphate free energy source, the absence of exogenous nucleoside triphosphates, the presence of nucleoside monophosphates, and exogenous organic phosphate.

ATP is required for protein synthesis in cell-free reactions. Traditionally, a compound with a high-energy phosphate bond, such as phosphoenolpyruvate (PEP), is added to the reaction for this purpose. However, since glycolytic enzymes are also present in the cell extract, glucose and other metabolic intermediates, such as glutamate, pyruvate, etc. can be used to drive cell-free reactions at a much lower cost, and with a higher potential for ATP generation utilizing methods that also activate oxidative phosphorylation. The reaction conditions that generate this more natural environment result from providing a combination of factors, as described below. This system is capable of significant protein production for up to 6 hours in an in vitro batch reaction. By mimicking the cellular environment, an enhanced synthetic capability is provided.

In preferred embodiments of the invention, a reaction mixture as described herein is used for in vitro synthesis of biological macromolecules by using glucose, glutamate, pyruvate, etc. as an energy source and by replacing the conventional exogenous nucleoside triphosphates with nucleoside monophosphates.

Improved yields are provided by the addition of exogenous phosphate, e.g. organic phosphate, etc. Usually phosphate is provided at a concentration of at least about 1 mM, preferably at least about 5 mM, and not more than about 20 mM, usually not more than about 15 mM, and preferably at about 10 mM. Useful sources of phosphate ($PO_4$) include a variety of salts and acids that are compatible with the biological reactions, e.g. potassium phosphate, magnesium phosphate, ammonium phosphate, etc. In an alternative embodiment, phosphate is provided by adding an appropriate amount of a compound containing phosphate such that small amounts of phosphate are released, e.g. by enzymatic release, during the reaction.

The reactions are preferably substantially free of polyethylene glycol. Performing synthesis in the substantial absence of polyethylene glycol allows for activation of oxidative phosphorylation and provides for improved folding; and may further be combined with, for example, the methods described in U.S. Pat. No. 6,548,276, herein incorporated by reference.

The methods of the present invention allow for production of proteins with the addition of an energy source to supplement synthesis, where the energy source is phosphate free, e.g. glucose, pyruvate, glutamate, etc. Sources include amino acids, e.g. glutamate, compounds in the tricarboxylic acid (TCA) cycle, citrate, cis-aconitate, isocitrate, α-ketoglutarate, succinyl-CoA, succinate, fumarate, malate, oxaloacetate, glyoxylate, glycerol, and other compounds that can be directed into central metabolism, such as acetate, etc. The energy source may be supplied in concentrations of at least about 10 mM, at least about 20 mM, more usually at least about 30 mM. Such compounds are not usually added in concentrations greater than about 250 mM, more usually not greater than about 150 mM. For example an energy source may be potassium glutamate, ammonium glutamate, and the like. In some embodiments a cocktail of sources is used, e.g. a mixture of potassium glutamate and ammonium glutamate; or a combination of glucose and glutamate sources, etc. Additional amounts of the energy source may be added to the reaction mixture during the course of protein expression, in order to extend reaction times. Alternatively, smaller initial concentrations followed by continuous or intermittent feeding may be employed.

In vitro synthesis, as used herein, refers to the cell-free synthesis of biological macromolecules in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc., and such co-factors, enzymes and other reagents that are necessary for the synthesis, e.g. ribosomes, tRNA, polymerases, transcriptional factors, etc. Such synthetic reaction systems are well-known in the art, and have been described in the literature. The cell free synthesis reaction may be performed as batch, continuous flow, or semi-continuous flow, as known in the art. The in vitro synthesis on biological macromolecules may include translation of MRNA to produce polypeptides or may include the transcription of mRNA from a DNA template.

The reactions preferably utilize cell extracts derived from bacterial cells grown in medium containing glucose and phosphate, where the glucose is present at a concentration of at least about 0.25% (weight/volume), more usually at least about 1%; and usually not more than about 4%, more usually not more than about 2%. An example of such media is 2YTPG medium, however one of skill in the art will appreciate that many culture media, particularly defined media, can be adapted for this purpose, as there are many published media suitable for the growth of bacteria such as $E.\ coli$, using both defined and undefined sources of nutrients (see Sambrook, J., E. F. Fritsch, and T. Maniatis. 1989. Molecular Cloning: A Laboratory Manual, $2^{nd}$ edition. Cold Spring Harbor University Press, Cold Spring Harbor, N.Y. for examples of glucose containing media).

The particular strain of bacteria, e.g. $E.\ coli$, utilized for the development of this new technology may be optimized. In particular, genetic modifications can be made to the strain that can enhance protein synthesis. For example, the strain utilized in the experiments described above had the speA, tnaA, sdaA, sdaB, tonA, and endA genes deleted from the chromosome. The first four mutations help to stabilize arginine, tryptophan, and serine concentrations in the reaction. The latter two mutations protect against bacteriophage infection and stabilize DNA within the system. Alternatively, metabolic inhibitors to undesirable enzymatic activity may be added to the reaction mixture.

While conventional reaction mixtures (for example, see Kim and Swartz, 2001) contain about 2% polyethylene glycol 8000, it is found that this diminishes the yield. In the present methods, the molecules spermidine and putrescine are used in the place of PEG. Spermine or spermidine is present at a concentration of at least about 0.5 mM, usually at least about 1 mM, preferably about 1.5 mM, and not more than about 2.5 mM. Putrescine is present at a concentration of at least about 0.5 mM, preferably at least about 1 mM, preferably about 1.5 mM, and not more than about 2.5 mM. These concentrations are highly dependent on the overall extract concentration used in the cell-free reaction. One skilled in the art will appreciate that upon altering extract concentrations, concentrations of spermidine an putrescine may also be altered to ranges outside those described here for typical reaction conditions.

The concentration of magnesium in the reaction mixture affects the overall synthesis. Often there is magnesium present in the cell extracts, which may then be adjusted with additional magnesium to optimize the concentration. Sources of magnesium salts useful in such methods are known in the art. In one embodiment of the invention, the source of magnesium may be magnesium glutamate. A preferred concentration of magnesium is at least about 5 mM, usually at least about 10 mM, and preferably a least about 12 mM; and at a concentration of not more than about 20 mM, usually not more than about 15 mM. The slight variation in glutamate concentration caused by the use of magnesium glutamate does not affect yields.

The system can be run under aerobic and anaerobic conditions. Oxygen may be supplied, particularly for reactions larger than 15 µl, in order to increase synthesis yields. The headspace of the reaction chamber can be filled with oxygen; oxygen may be infused into the reaction mixture; etc. Oxygen can be supplied continuously or the headspace of the reaction chamber can be refilled during the course of protein expression for longer reaction times. Other electron acceptors, such as nitrate, sulfate, or fumarate may also be supplied in conjunction with preparing cell extracts so that the required enzymes are active in the cell extract.

It is not necessary to add exogenous cofactors. Compounds such as nicotinamide adenine dinucleotide (NADH), $NAD^+$, or Coenzyme A may be used to supplement protein synthesis yields but are not required.

The template for cell-free protein synthesis is preferably DNA. Coupled transcription and translation, generally utilized in $E.\ coli$, systems, continuously generates mRNA from a DNA template with a recognizable promoter. Either endogenous RNA polymerase is used, or an exogenous phage RNA polymerase, typically T7 or SP6, is added directly to the reaction mixture. Alternatively, mRNA can be continually amplified by inserting the message into a template for QB replicase, an RNA dependent RNA polymerase. Nucleases can be removed from extracts to help stabilize mRNA levels. The template can encode for any particular gene of interest.

Other salts, particularly those that are biologically relevant, such as manganese, may also be added. Potassium is generally present at a concentration of at least about 50 mM, and not more than about 250 mM. Ammonium may be present, usually at a concentration of not more than 200 mM, more usually at a concentration of not more than about 100 mM, and preferably at a concentration of not more than about 20 mM. Usually, the reaction is maintained in the range of about pH 5-10 and a temperature of about 20°-50° C.; more usually, in the range of about pH 6-9 and a temperature of about 25°-40° C. These ranges may be extended for specific conditions of interest.

Vesicles, either purified from the host organism (see Muller and Blobel (1984) "In vitro translocation of bacterial proteins across the plasma membrane of $Escherichia\ coli$", PNAS 81:7421-7425) or synthetic, may also be added to the system. These may be used to enhance protein synthesis and folding. The technology described herein has been shown to activate the oxidative phosphorylation process that utilizes cytoplasmic membrane components. Inverted membrane vesicles containing respiratory chain components and the $F_1F_0$ATPase must be present for the activation of oxidative phosphorylation. The present methods also may be used for cell-free reactions to activate other sets of membrane proteins; for example, to insert or translocate proteins or to translocate other compounds.

In the glucose system, the buffer is important for pH stabilization. For example, bis-Tris buffer in a glucose reaction may be present at from about 10 to 150 mM, usually about 50 mM. Other buffers could also be used as long as their pKa is appropriate for the reaction (probably between 6.8 and 7.2). The pH can also be stabilized through direct addition of base during the reaction.

Methods for Enhanced In Vitro Synthesis

Synthetic systems of interest include systems for the replication of biopolymers, which can include amplification of DNA, transcription of RNA from DNA or RNA templates, translation of RNA into polypeptides, and the synthesis of complex carbohydrates from simple sugars. Enhanced synthesis may include increases in the total or relative amount of polypeptide synthesized in the system; increases in the total or relative amount of polypeptide synthesized per unit of time; increases in the total or relative amount of biologically active polypeptide synthesized in the system; increases in the total or relative amount of soluble polypeptide synthesized in the system, and the like.

The reactions may utilize a large scale reactor, small scale, or may be multiplexed to perform a plurality of simultaneous syntheses. Continuous reactions will use a feed mechanism to introduce a flow of reagents, and may isolate the end-product as part of the process. Batch systems are also of interest, where additional reagents may be introduced to prolong the period of time for active synthesis. A reactor may be run in any mode such as batch, extended batch, semi-batch, semi-continuous, fed-batch and continuous, and which will be selected in accordance with the application purpose.

The reactions may be of any volume, either in a small scale, usually at least about 1 µl and not more than about 15 µl, or in a scaled up reaction, where the reaction volume is at least about 15 µl, usually at least about 50 µl, more usually at least about 100 µl, and may be 500 µl, 1000 µl, or greater. In most cases, individual reactions will not be more than about 10 ml, although multiple reactions can be run in parallel. However, in principle, reactions may be conducted at any scale as long as sufficient oxygen (or other electron acceptor) is supplied.

Of particular interest is the translation of mRNA to produce proteins, which translation may be combined with in vitro synthesis of mRNA from a DNA template. Such a cell-free system will contain all factors required for the translation of mRNA, for example ribosomes, amino acids, tRNAs, aminoacyl synthetases, elongation factors, initiation factors, and ribosome recycling factors. Cell-free systems known in the art include $E.$ $coli$ extracts, etc., which can be treated with a suitable nuclease to eliminate active endogenous mRNA.

In addition to the above components such as cell-free extract, genetic template, and amino acids, materials specifically required for protein synthesis may be added to the reaction. These materials include salt, folinic acid, cyclic AMP, inhibitors for protein or nucleic acid degrading enzymes, inhibitors or regulators of protein synthesis, adjusters of oxidation/reduction potential(s), non-denaturing surfactants, buffer components, spermine, spermidine, putrescine, etc.

The salts preferably include potassium, magnesium, and ammonium salts (e.g. if acetic acid or sulfuric acid). One or more of such salts may have amino acids as a counter anion, e.g. glutamic acid. There is an interdependence among ionic species for optimal concentration. These ionic species are typically optimized with regard to protein production. When changing the concentration of a particular component of the reaction medium, that of another component may be changed accordingly. For example, the concentrations of several components such as nucleotides and energy source compounds may be simultaneously controlled in accordance with the change in those of other components. Also, the concentration levels of components in the reactor may be varied over time. The adjuster of oxidation/reduction potential may be dithiothreitol, ascorbic acid, glutathione and/or their oxidized forms. Also, a non-denaturing surfactant such as Triton X-100 is optionally included, at a concentration of not more than about 500 mM, more usually not more than about 250 mM.

When using a protein isolating means in a continuous operation mode, the product output from the reactor flows through a membrane and into the protein isolating means. In a semi-continuous operation mode, the outside or outer surface of the membrane is put into contact with predetermined solutions that are cyclically changed in a predetermined order. These solutions contain substrates such as amino acids and nucleotides. At this time, the reactor is operated in dialysis, diafiltration batch or fed-batch mode. A feed solution may be supplied to the reactor through the same membrane or a separate injection unit. Synthesized protein is accumulated in the reactor, and then is isolated and purified according to the usual method for protein purification after completion of the system operation.

Where there is a flow of reagents, the direction of liquid flow can be perpendicular and/or tangential to a membrane. Tangential flow is effective for recycling ATP and for preventing membrane plugging and may be superimposed on perpendicular flow. Flow perpendicular to the membrane may be caused or effected by a positive pressure pump or a vacuum suction pump. The solution in contact with the outside surface of the membrane may be cyclically changed, and may be in a steady tangential flow with respect to the membrane. The reactor may be stirred internally or externally by proper agitation means.

During protein synthesis in the reactor, the protein isolating means for selectively isolating the desired protein may include a unit packed with particles coated with antibody molecules or other molecules immobilized with a component for adsorbing the synthesized, desired protein, and a membrane with pores of proper sizes. Preferably, the protein isolating means comprises two columns for alternating use.

The amount of protein produced in a translation reaction can be measured in various fashions. One method relies on the availability of an assay that measures the activity of the particular protein being translated. An example of an assay for measuring protein activity is a luciferase assay system, or chloramphenical acetyl transferase assay system. These assays measure the amount of functionally active protein produced from the translation reaction. Activity assays will not measure full length protein that is inactive due to improper protein folding or lack of other post translational modifications necessary for protein activity.

Another method of measuring the amount of protein produced in coupled in vitro transcription and translation reactions is to perform the reactions using a known quantity of radiolabeled amino acid such as $^{35}$S-methionine, $^{3}$H-leucine or $^{14}$C-leucine and subsequently measuring the amount of radiolabeled amino acid incorporated into the newly translated protein. Incorporation assays will measure the amount of radiolabeled amino acids in all proteins produced in an in vitro translation reaction including truncated protein products. The radiolabeled protein may be further separated on a protein gel, and by autoradiography confirmed that the product is the proper size and that secondary protein products have not been produced.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

Glucose as an Energy Source

Methods and Materials

The standard Cytomim environment for synthesis, contains the following components: 1.2 mM ATP, 0.85 mM each of GTP, UTP and CTP, 1 mM DTT, 130 mM potassium glutamate, 10 mM ammonium glutamate, 8 mM magnesium glutamate, 34 µg/ml folinic acid, 170.6 µg/ml E. coli, tRNA mixture, 13.3 µg/ml plasmid, 100 µg/ml T7 RNA polymerase, 2 mM each of 20 unlabeled amino acids, 11 µM [$^{14}$C]leucine, 1.5 mM spermidine and 1 mM putrescine, 0.33 mM nicotinamide adenine dinucleotide, 0.26 mM Coenzyme A, 2.7 mM sodium oxalate and 0.24 volumes of S30 extract. Prokaryotic cell-free protein synthesis is performed using a crude S30 extract derived from Escherichla coli K12 (strain KC1 described in Michel-Reydellet et al (2004) Met Eng (6)197-203, genotype A19 ΔtonA ΔtnaA ΔspeA ΔendA ΔsdaA ΔsdaB met+), with slight modifications from the protocol of Pratt, J. M. 1984. (Coupled transcription-translation in prokaryotic cell-free systems. In Transcription and translation: a practical approach. Hanes, B. D., and S. J. Higgins. (Eds.). p. 179-209. IRL Press, New York.) Cells for the extract are grown with defined media (Zawada et al. (2003). High-density, defined media culture for the production of Escherichia coli cell extracts. In: Saha B, editor. Fermentation Biotechnology. Washington, D.C.: ACS Press. p 142-156). T7 RNA polymerase was prepared from E. coli, strain BL21 (pAR1219) according to the procedures of Davanloo et al. 1984 (Cloning and expression of the gene for bacteriophage T7 RNA polymerase. Proc Nat'l Acad. Sci. USA 81:2035-2039.) The system can be enhanced with the addition of 33 mM sodium pyruvate, although this is not necessary. There was approximately an additional 3.3 mM magnesium, 14.4 mM potassium, 2.4 mM TRIS, and 23.5 mM acetate in each reaction originating from the cell extract.

The modified Cytomim environment for synthesis, according to the methods of the present invention, is as follows: 10 mM potassium phosphate and 50 mM Bis-Tris (pH 7.0) was added, 5 µM of [$^{14}$C]leucine was used instead of 11 µM. In addition, 30 mM glucose was added, 1.2 mM AMP was substituted for 1.2 mM ATP, and 0.85 mM each of GMP, UMP, and CMP were substituted for 0.85 mM each of GTP, UTP, and CTP. Additionally, oxalic acid was omitted.

Reactions were incubated at 37° C. for 3-6 hours. The amount of synthesized protein is estimated from the measured TCA-insoluble radioactivities using a liquid scintillation counter (Beckman LS3801). (Kim et al. 1996). Soluble protein yields were determined as previously described (Kim and Swartz 2000).

Results

The standard reaction mixture for a coupled transcription-translation reaction is described by Kim and Swartz (2001). The energy source in the standard reaction is phosphoenolpyruvate (PEP). Previous direct substitution of PEP with glucose resulted in virtually no protein synthesis. However, when PEP was replaced by glucose-6-phosphate (G6P) significant protein yields of 228±13 µg/mL were observed (Kim and Swartz 2001). Glucose-6-phosphate is only one-step away from glucose in the glycolysis reaction pathway, suggesting that the initial phosphorylation step may be limiting. Several experiments were conducted to alleviate this limitation including the addition of hexokinase or glucokinase to the reaction or slowly feeding glucose. Neither approach was successful.

The G6P reaction continued to be optimized by modifications of the standard reaction mixture until protein yields using this energy source averaged over 700 µg/mL. To obtain these protein yields, a new pH buffer was used, and oxalic acid was removed. In addition, it was shown that NTPs could be replaced by NMPs in the G6P reaction giving similar yields. This substitution dramatically decreased the reaction cost. Despite these advances, the optimized conditions still did not allow significant protein synthesis when G6P was replaced with glucose.

Glucose was successfully used as an energy source with NMPs when polyethylene glycol was replaced with the natural cations putrescine and spermidine and when additional phosphate was added to the optimized reaction, and when sodium oxalate was omitted. Phosphate is important both for the initial step of glycolysis (glucose to G6P) and for phosphorylation of the NMPs to NTPs. The cell-free reaction was phosphate-limited when using glucose as an energy source. This limitation did not exist in traditional cell-free reactions that typically utilize a phosphorylated energy source such as PEP, creatine phosphate, or even G6P. It was found that experiments using glucose plus phosphate gave protein yields of over 400 µg/mL, as compared to the experiments using G6P, which produced protein yields over 800 µg/mL. Glucose and NMP reactions are beneficial because of the decreased costs and increased stability of these reagents.

Figure 1:
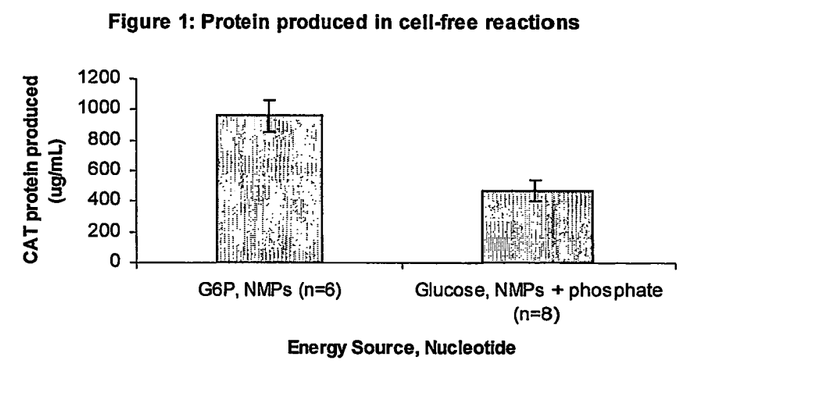
FIG. 1 is a bar graph comparing the level of in vitro protein synthesis with the component system of the present invention using an energy source as indicated and nucleoside monophosphates plus phosphate. CAT expression was determined from $^{14}$C-leucine incorporation. Error bars represent the range from two separate experiments.

Pyruvate, another nonphosphorylated energy source, was also used successfully in a cell-free protein synthesis reaction with NMPs only when additional phosphate was added. A three hour batch reaction of the mixture described above was carried out after replacing glucose with pyruvate and NTPs with NMPs. Phosphate optimization resulted in protein yields that are close to the amount obtained for NTPs (FIG. 1) at a fraction of the cost. Without any additional phosphate, protein synthesis yields are substantially lower.

Figure 2:
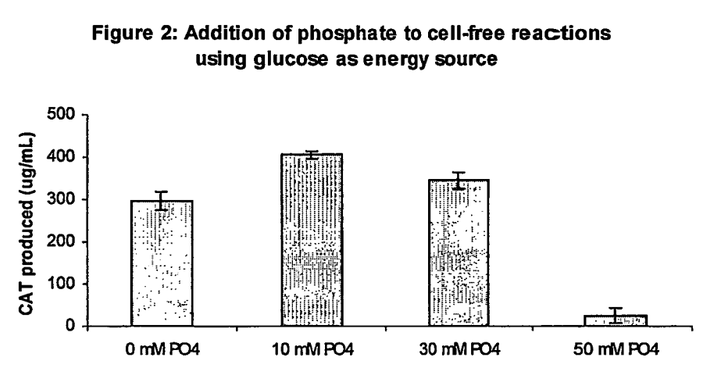
FIG. 2 is a bar graph comparing the level of in vitro protein synthesis with the component system of the present invention using glucose as an energy source with nucleoside triphosphates and varying amounts of phosphate. CAT expression was determined from $^{14}$C-leucine incorporation. Error bars represent the standard deviation from three separate experiments.
Figure 3:
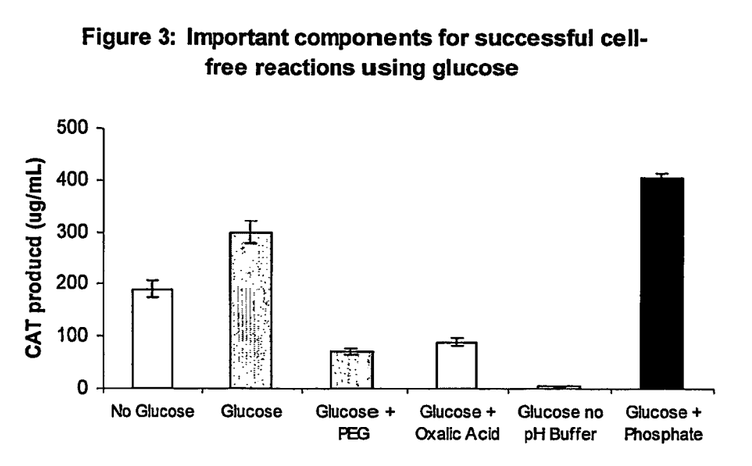
FIG. 3 is a bar graph comparing the level of in vitro protein synthesis with the component system of the present invention using glucose as an energy source and various components for successful cell-free reactions. CAT expression was determined from $^{14}$C-leucine incorporation. Error bars represent the standard deviation from three separate experiments.

To further determine the requirements for this new reaction, reaction components were investigated individually. It was determined that reactions that use NTPs and glucose as an energy source also benefit from additional phosphate (FIG. 2), resulting in similar yields to the NMP reaction. Further experiments were also conducted to determine other steps that are important for successful reactions. It was found that removal of PEG and oxalic acid, as well as careful pH control through the use of the appropriate buffer had a significant impact on protein yields (FIG. 3).

Previously, cell-free protein synthesis reactions were limited to using phosphorylated energy sources and nucleotide triphosphates. These compounds are relatively expensive reagents in the cell-free reactions. In addition, the phosphorylated molecules are more susceptible to degradation and create a variable reaction environment with respect to inorganic phosphate concentration. Using glucose and nucleotide monophosphates will increase the reaction robustness and homeostasis while also dramatically decreasing costs. In fact, when the costs of energy sources and nucleotides are compared, glucose and NMPs are nearly two orders of magnitude less expensive than PEP and NTPs (Table 1, Row 1).

Protein synthesis yields of in vitro synthesis reactions using glucose as an energy source and NMPs are approximately 60% of the traditional reaction. However, the great cost advantage of using glucose and NMPs compensates for the slight decrease in yield such that the relative product yield is almost ninety times better on a cost basis (Table 1, Row 3).

TABLE 1

Comparison of cell-free reactions with various energy sources and nucleotides

| | NTPs | | | NMPs (+phosphate) | | |
|---|---|---|---|---|---|---|
| | PEP | G6P | Glucose | PEP | G6P | Glucose |
| Cost of energy source and nucleotides ($/mL reaction) | 1.88 | 0.73 | 0.61 | 1.28 | 0.13 | 0.0108 |
| Typical yields (µg/mL) | 700 | 800 | 430 | 700 | 960 | 470 |
| Relative product yield (µg protein/$) | 1 | 2.9 | 1.9 | 1.5 | 19.6 | 116 |

Additional cell-free reactions were carried out as described above with respect to reaction conditions, using the *E. coli* strain KC1 as the source of extract (described by Michel-Reydellet et al (2004) Metab Eng 6(3):197-203). The data for ATP concentration was obtained by taking samples at various times during a cell-free reaction. The sample is precipitated with equal volume (1:1) of 5% trichloroacetic acid (TCA) and centrifuged for 10 min at 14000 g. The supernatant is collected and analyzed in a firefly luciferase assay to determine ATP concentration (Kim and Swartz (2001), supra.)

Figure 4:
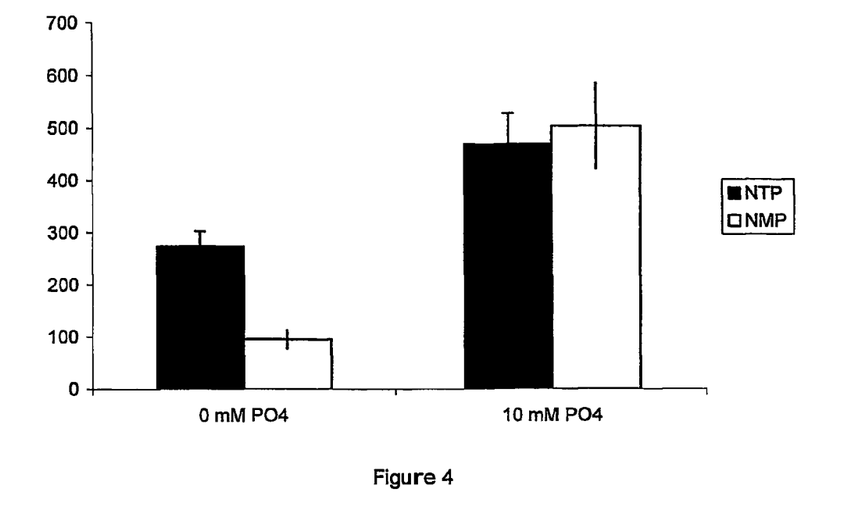
FIG. 4: Effect of additional 10 mM phosphate on cell-free protein synthesis reactions using glucose as an energy source with either NTPs or NMPs. Error bars represent the standard deviation from nine experiments (n=9).

FIG. 4 is a comparison of the glucose system as described above, with NMPs and NTPS with or without phosphate. The data in FIG. 4 demonstrate that 10 mM phosphate is beneficial for the glucose system. In addition, these data show that NMPs can replace NTPs without an impact on protein synthesis yields.

Figure 5:
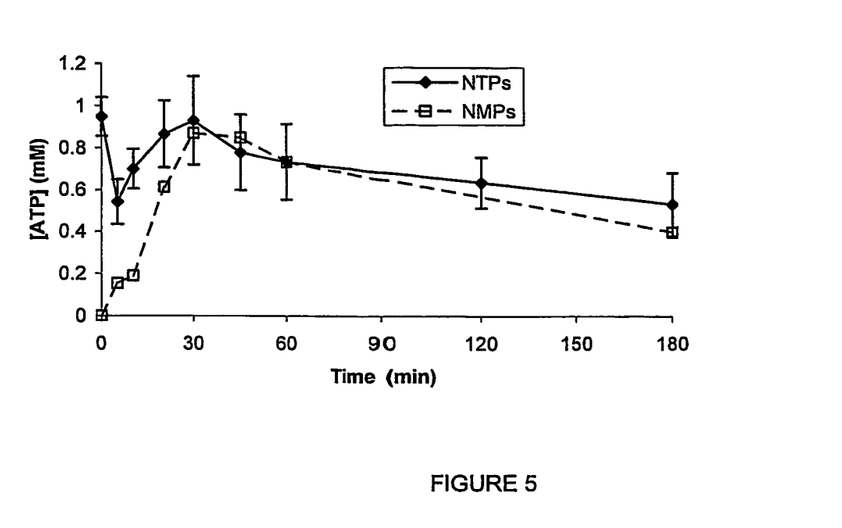
FIG. 5: ATP concentration in cell-free reactions that use glucose as an energy source with NTPs or NMPs. Error bars represent the standard deviation of three experiments (n=3).

The data in FIG. 5 show that the cell-free system using NMPs can regenerate the ATP necessary for transcription/translation. In fact, the ATP concentration with NMPs quickly reaches the same level as is seen in the glucose/NTP reaction.

Example 2

Glutamate as an Energy Source

The reaction mixture for combined transcription-translation reactions described below contains the following components: 1.2 mM ATP, 0.85 mM each of GTP, UTP and CTP, 130 mM potassium glutamate, 10 mM ammonium glutamate, 10 mM magnesium glutamate, 1.5 mM spermidine, 1 mM putrescine, 34 µg/ml folinic acid, 170.6 µg/ml *E. coli*, tRNA mixture, 13.3 µg/ml plasmid, 100 µg/ml T7 RNA polymerase, 2 mM each of 20 unlabeled amino acids, 5 µM L-[U-$^{14}$C]-leucine, 0.33 mM nicotinamide adenine dinucleotide, 0.26 mM Coenzyme A, 4.0 mM sodium oxalate and 0.24 volumes of S30 extract.

Pyruvate was omitted as an energy source. In this situation, supplementation with 10 mM potassium phosphate, pH 7.2 (with glacial acetic acid), is beneficial for protein expression. In addition to using NTPs (ATP, GTP, UTP, and CTP), reactions can also be performed with NMPs (AMP, GMP, UTP, and CMP) at the same stating concentrations as described above. There is approximately 3.3 mM magnesium, 14.4 mM potassium, 2.4 mM TRIS: pH 8.2, and 23.5 mM acetate in each reaction originating from the cell extract. The extract makes up 24% of the reaction volume, and it is in its own buffer made of magnesium, potassium, and tris acetate. Therefore this buffer increases the concentration of these items when it is added to the reaction. The concentrations given above (3.3 mM, 14.4 mM etc) are the final concentrations after the extract is already added. *E. coli*, total tRNA mixture is purchased from Roche Molecular Biochemicals (Indianapolis, Ind.). L-[U-$^{14}$C]-leucine is from Amersham Pharmacia Biotechnology (Uppsala, Sweden). All other reagents are obtained from Sigma (St. Louis, Mo.).

The cell-free protein synthesis reaction was performed by using a crude $30 extract derived from *E. coli*, K12 (strain KC1, genotype A19 ΔtonA ΔtnaA ΔspeA ΔendA ΔsdaA ΔsdaB met$^+$). Extract preparation was performed as described previously (Swartz et al. (2004). Cell-free protein synthesis with prokaryotic coupled transcription-translation. In: Balbas P, Lorence A, editors. Recombinant Protein Protocols: Methods in Molecular Biology Series: Volume 267. Totowa, N. J.: Humana Press Inc. p. 169-182). Plasmid pK7CAT was used as a template for protein synthesis. pk7CAT encodes for the sequence of chloramphenicol acetyl transferase (CAT) using the T7 promoter and terminator. T7 polymerase, prepared as described by Swartz et al. (2004), was added to the reaction. The amount of synthesized protein is calculated from the measured TCA-insoluble radioactivities using a liquid scintillation counter and by enzymatic activity (Shaw (1975) Methods Enzymol. 43:737-755).

Figure 6:
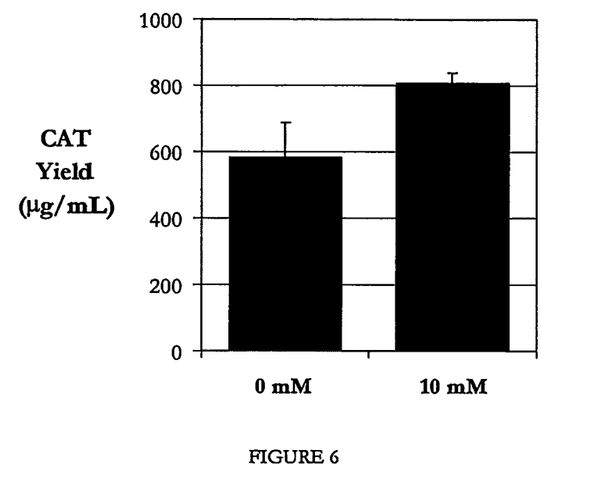
FIG. 6. Expression of CAT using the Cytomim system with or without phosphate addition. Reactions (15 µL) were carried out for 6 hours and CAT expression was determined by $^{14}$C-leucine incorporation. Error bars represent the standard deviation for eleven individual experiments. All of the reactions were performed using the Cytomim system without sodium pyruvate and with NTPs. Phosphate concentrations are indicated on the x-axis.

Phosphate supplementation is shown herein to significantly benefit protein production yields in the Cytomin system energized by glutamate metabolism and oxidative phosphorylation. This is described in the context of using NTPs or NMPs. For the case of NPTs, we observed a significant increase in chloramphenicol acetyl transferase (CAT) production (as assessed by $^{14}$C-leucine incorporation) after a 6-hour expression relative to reactions without phosphate addition (FIG. 6). Phosphate addition increased yields when nucleoside triphosphates were employed as well.

To optimize CAT expression in the glutamate/phosphate system, the effect of phosphate concentration on Cytomim cell-free reactions (without sodium pyruvate) was tested. Chloramphenicol acetyl transferase (CAT) production was assessed by $^{14}$C-leucine incorporation after a 6-hour expression over a range of initial phosphate concentrations. The most favorable yields of CAT were observed with the addition of 10 mM phosphate (Table 2).

TABLE 2

Table 1 - Phosphate optimization studies in the Cytomim system based on relative total CAT expression. All experiments were run using the conditions from the Cytomim system without sodium pyruvate and with NTPs. Fifteen microliter reactions were incubated at 37° C. for 6 hours. Potassium phosphate (dibasic, Mallinckrodt: Phillipsburg, NJ), adjusted to pH 7.25 with glacial acetic acid, was used.

| Added Phosphate (mM) | Relative CAT Production |
|---|---|
| 0 | 0.50 ± 0.10 |
| 4 | 0.74 ± 0.13 |
| 8 | 0.86 ± 0.04 |
| 10 | 1.00 ± 0.08 |
| 12 | 0.99 ± 0.05 |
| 16 | 0.93 ± 0.05 |

Figure 9:
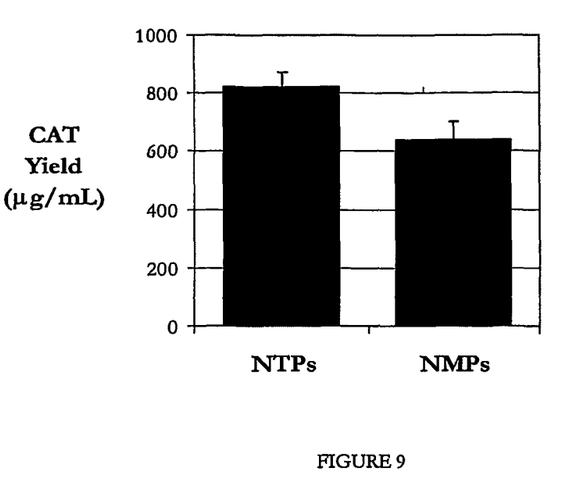
FIG. 9 CAT expression was measured with either NMPs or NTPs at the standard initial concentrations. Protein synthesis reactions were carried out for 6 hours and samples were taken to quantify CAT accumulation.

To quantify the impact of exchanging NMPs for NTPs, CAT expression was measured in the new system (glutamate/10 mM phosphate) with either NMPs or NTPs at the standard initial concentrations. Protein synthesis reactions were carried out for 6 hours and samples were taken to quantify CAT accumulation. A 22% decrease in CAT yields using NMPs relative to NTPs was observed (FIG. 9). While the overall protein yields are reduced, the cost benefit of using the nucleoside monophosphates results in a significantly higher production yield (milligrams of protein per dollar for energy source and nucleotides) as compared to reactions with NTPs (Table 3).

Figure 10:
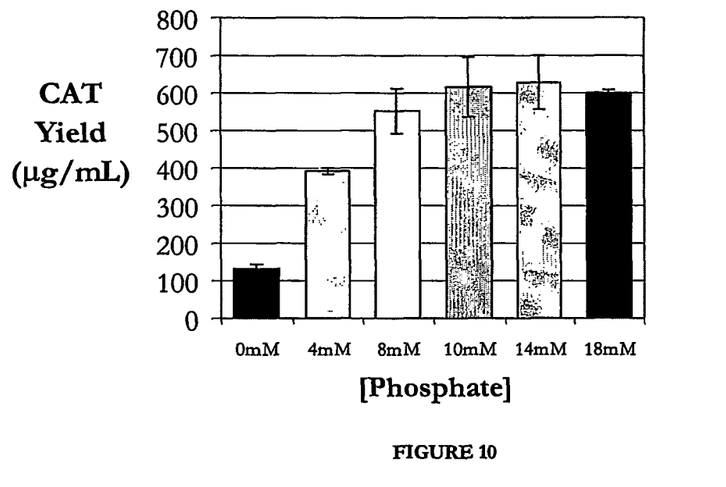
FIG. 10. Phosphate optimization studies in the Cytomim system based on relative total CAT expression. All experiments were run using the conditions from the Cytomim system without sodium pyruvate and with NMPs. Fifteen microliter reactions were incubated at 37° C. for 6 hours. Potassium phosphate (dibasic, Mallinckrodt: Phillipsburg, N.J.), adjusted to pH 7.25 with glacial acetic acid, was used.

The effect of a range of phosphate concentrations on protein expression yields in the NMP reactions was also examined. In agreement with previous data demonstrating that cell-free protein synthesis reactions exploiting NMPs are phosphate limited, phosphate supplementation was critical for high yields. The optimum phosphate concentration was 10 mM. Upon addition of 10 mM phosphate, yields increased more than 400% relative to cell-free reactions without phosphate (FIG. 10).

TABLE 3

I updated these numbers with the current prices. Now they match with Table 1

| System | Reaction size | Energy source and nucleotides | Synthesis duration (Hr) | CAT produced (mg/mL) | Energy source and nucleotides cost ($/mL reaction) | mg protein/ ($ energy source and nucleotides) |
|---|---|---|---|---|---|---|
| PANOx-SP | 15 μL | PEP, NTPs | 3 | 0.70 | 1.88 | 0.37 |
| Cytomim | 15 μL | Glutamate, Phosphate, NTPs | 6 | 0.80 | 0.61 | 1.31 |
| Cytomim | 15 μL | Glutamate, Phosphate, NMPs | 6 | 0.62 | 0.0104 | 59 |

Table 3 - Product yields (mg protein/$ energy source and nucleotide cost) for the PANOx-SP (with NTPs), Cytomim (without pyruvate, with phosphate and NTPs) and Cytomim (without pyruvate, with phosphate and NMPs) systems.

Figure 7:
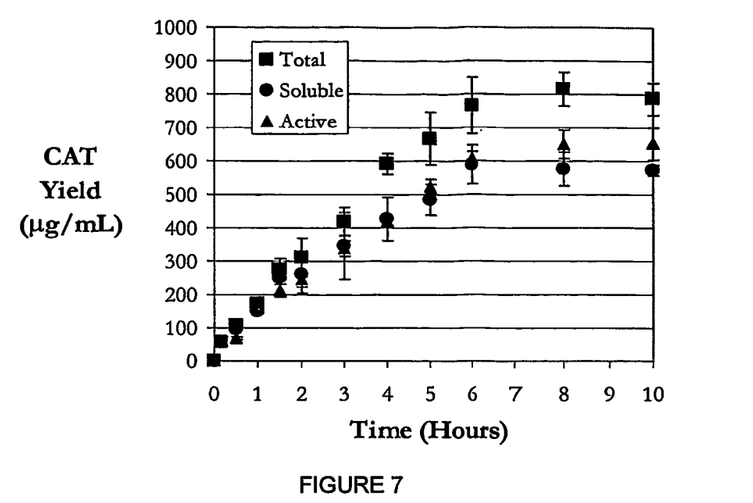
FIG. 7. CAT Expression over time using the Cytomim system (w/NTPs) without pyruvate and with 10 mM additional phosphate. Reactions were carried out for 6 hours at 37° C. and CAT expression was determined by $^{14}$C-leucine incorporation and enzymatic activity assay. Fifteen microliter reaction mixtures were prepared in a different tube for each time point. At each time point, one tube was sacrificed in order to determine the amount of expressed protein. Error bars represent the standard deviation for seven separate experiments. (■) Total yield of CAT as monitored by $^{14}$C-leucine incorporation in the Cytomim system. (●) Soluble yield of CAT as monitored by $^{14}$C-leucine incorporation in the Cytomim system. (▲) Active yield of CAT as determined by enzymatic assay.

To further characterize this new approach exploiting glutamate metabolism, NTPs, and phosphate supplementation, CAT accumulation over time was quantified as determined by TCA precipitable radioactivity and enzymatic activity. The final yield of CAT after a six-hour incubation was 802±48 μg/ml (FIG. 7). The soluble and active fraction of CAT was approximately 70±3% (FIG. 2). Due to the low cost of potassium phosphate addition ($0.00016/mL reaction volume for 10 mM potassium phosphate), protein production yields supplemented with 10 mM phosphate are increased by 33% without impacting the raw materials cost of the reaction.

Figure 8:
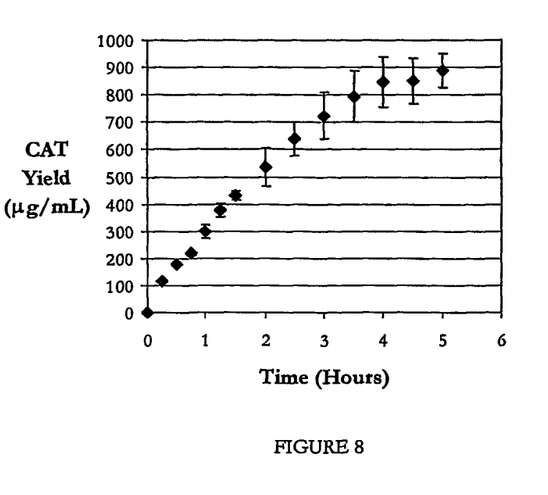
FIG. 8. Expression of CAT using the Cytomim system without pyruvate and with 10 mM phosphate in a 1 mL bubble column. Reactions (1 mL) were carried out for 5 hours at 37° C. CAT expression was determined by $^{14}$C-leucine incorporation. Error bars represent the high and low of two individual experiments. At approximately 3.5 hours, the reactor began to foam out, subsequent addition of $1\times10^{-4}$ (v/v) of Sigma 0-30 antifoam controlled this problem.

To demonstrate the utility of the new glutamate and phosphate system, 1 mL jacketed bubble column reactions were performed. Combined transcription and translation reactions, maintained at 37° C., were carried out for 5 hours using the Cytomim conditions (without pyruvate, with NTPs and supplemented with 10 mM phosphate), except that the reaction was supplemented with 0.007% (v/v) Sigma 0-30 antifoam. This agent was used to control foaming. In addition, pure oxygen bubbles, approximately 0.25 cm in diameter, were supplied to the bottom of the cell-free reaction chamber at a rate of 2 bubbles per second to deliver the oxygen necessary for ATP regeneration. At each time point, samples were taken to quantify the amount of total CAT, which was determined by $^{14}$C-leucine incorporation. FIG. 8 shows the average CAT accumulation (~900 μg/mL) from two separate experiments. Relative to 15 μL batch reactions (FIG. 7), the bubble column format has a faster rate of protein synthesis.

Here, phosphate supplementation has been shown to increase protein synthesis yields by 33% in a cell-free protein synthesis reaction energized by glutamate. In addition to increasing the utility of this system by enhancing yields, this enhances yields without affecting the overall economics of the raw materials (reagent cost). In particular, cell-free reactions energized by glutamate metabolism increase more than 4-fold relative to reactions without phosphate.

As a result of the yield increase from phosphate supplementation, the two dominant reagent costs (energy substrates and nucleotides) associated with cell-free reagents can be reduced by more than two-orders of magnitude (160-fold increase (59/0.37)) from the conventional PANOx-SP approach by using cell-free reactions energized by glutamate metabolism and oxidative phosphorylation with supplementation of modest phosphate concentrations and substitution of NMPs for NTPs (Table 3). These results demonstrate the economic viability of cell-free rDNA protein synthesis. It is not necessary to add exogenous cofactors for this new technology. Compounds such as nicotinamide adenine dinucleotide (NADH), $NAD^+$, or acetyl-coenzyme A can be used to supplement protein synthesis yields but are not required.

What is claimed is:
1. A method for synthesis of polynucleotides and/or polypeptides in a cell-free reaction mixture initially comprising a bacterial cell extract; a template for production of the polynucleotides and/or polypeptide; monomers for the polynucleotides and/or polypeptide to be synthesized, and such co-factors, enzymes and other reagents that are necessary for the synthesis; the method comprising:

synthesizing said polynucleotides and/or polypeptides in a cell-free reaction mixture modified to include:

at least 10 mM of a phosphate-free energy source wherein said phosphate free energy source is glucose or glutamate; nucleoside monophosphates in the absence of exogenous nucleoside triphosphates; and exogenous inorganic phosphate salts at a concentration of at least about 1 mM.

2. The method of claim 1, wherein the exogenous inorganic phosphate is provided at a concentration of from about 1 mM to about 20 mM.

3. The method of claim 1, wherein said phosphate is provided as potassium phosphate, magnesium phosphate, or ammonium phosphate.

4. The method of claim 1, wherein said synthesis comprises translation of mRNA to produce polypeptides.

5. The method of claim 4, wherein said synthesis also comprises transcription of mRNA from a DNA template.

6. The method of claim 1, wherein said synthesis of polynucleotides and/or polypeptides is performed as a batch reaction.

7. The method of claim 1, wherein said synthesis of polynucleotides and/or polypeptides is performed as a continuous reaction.

8. The method of claim 1, wherein said reaction mix comprises an extract from *E. coli* grown in glucose containing medium.

9. The method of claim 8, wherein said *E. coli* are grown in glucose and phosphate containing medium.

10. The method of claim 1, wherein said reaction mix comprises magnesium at a concentration of from about 5 mM to about 20 mM.

11. The method of claim 1, wherein said reaction mix is substantially free of polyethylene glycol.

12. The method according to claim 11, wherein said reaction mix comprises one or more of spermine, spermidine and putrescine.

13. The method of claim 1, wherein the reaction mixture yields over 400 µg/mL of the synthesized polypeptide.

* * * * *